US012611263B2

(12) United States Patent
Abbas et al.

(10) Patent No.: US 12,611,263 B2
(45) Date of Patent: Apr. 28, 2026

(54) MODULAR STEERABLE SHEATH AND CATHETER

(71) Applicant: Biosense Webster (Israel) Ltd.,
Yokneam (IL)

(72) Inventors: Mohammad Abbas, Orange, CA (US);
Mark Stanley, Irvine, CA (US); **Kokou
Anani Mawuena Amefia**, Aliso Viejo,
CA (US); Matthew W. Hitzeroth,
Irwindale, CA (US); **Justin Lee
Rumoro**, Chicago, IL (US)

(73) Assignee: Biosense Webster (Israel) Ltd.,
Yokneam (IL)

( * ) Notice: Subject to any disclaimer, the term of this
patent is extended or adjusted under 35
U.S.C. 154(b) by 288 days.

(21) Appl. No.: 18/477,418

(22) Filed: Sep. 28, 2023

(65) Prior Publication Data

US 2025/0107853 A1 Apr. 3, 2025

(51) Int. Cl.
| | |
|---|---|
| *A61B 34/20* | (2016.01) |
| *A61B 18/00* | (2006.01) |
| *A61B 18/14* | (2006.01) |

(52) U.S. Cl.
CPC .......... *A61B 34/20* (2016.02); *A61B 18/1492*
(2013.01); *A61B 2018/00351* (2013.01); *A61B
2018/00577* (2013.01); *A61B 2018/00839*
(2013.01); *A61B 2034/2051* (2016.02); *A61B
2217/007* (2013.01)

(58) Field of Classification Search
CPC ................ A61B 34/20; A61B 18/1492; A61B
2034/2051; A61B 2018/00351; A61B
2018/00577; A61B 2018/00839; A61B
2217/007
See application file for complete search history.

(56) References Cited

U.S. PATENT DOCUMENTS

| | | | |
|---|---|---|---|
| 5,391,199 A | 2/1995 | Ben-Haim | |
| 5,443,489 A | 8/1995 | Ben-Haim | |
| 5,558,091 A | 9/1996 | Acker et al. | |
| 5,738,096 A | 4/1998 | Ben-Haim | |
| 6,172,499 B1 | 1/2001 | Ashe | |
| 6,239,724 B1 | 5/2001 | Doron et al. | |

(Continued)

OTHER PUBLICATIONS

Extended European Search Report and Opinion dated Feb. 12, 2025,
from corresponding European Application No. 24203086.4.

*Primary Examiner* — Linda C Dvorak
*Assistant Examiner* — Abigail Bock

(57) ABSTRACT

A modular catheter system includes a guiding sheath and
multiple catheter inserts configured to couple to the guiding
sheath. The guiding sheath can include a navigation sensor
coupled to a distal portion of the guiding sheath shaft. A
location of a distal portion of a respective catheter insert can
be determined based on electrical signals from the naviga-
tion sensor. The catheter insert can be electrically coupled to
the guiding sheath to provide electrical connection to an
electrode assembly on the distal portion of the respective
catheter insert. The guiding sheath may include a deflection
mechanism that deflects the distal portion of the guiding
sheath and a distal portion of a catheter shaft of the catheter
insert. The modular catheter system may be configured to be
tracked and moved without the catheter inserts requiring a
navigation sensor or a deflection mechanism.

20 Claims, 8 Drawing Sheets

(56)         References Cited

U.S. PATENT DOCUMENTS

| | | | |
|---|---|---|---|
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 6,788,967 | B2 | 9/2004 | Ben-Haim et al. |
| 6,892,091 | B1 | 5/2005 | Ben-Haim et al. |
| 7,536,218 | B2 | 5/2009 | Govari et al. |
| 7,756,576 | B2 | 7/2010 | Levin |
| 7,848,787 | B2 | 12/2010 | Osadchy |
| 7,869,865 | B2 | 1/2011 | Govari et al. |
| 8,456,182 | B2 * | 6/2013 | Bar-Tal .................. A61B 5/283 600/509 |
| 9,480,416 | B2 | 11/2016 | Govari et al. |
| 9,907,480 | B2 | 3/2018 | Basu et al. |
| 2002/0133149 | A1 | 9/2002 | Bessette |
| 2013/0282007 | A1 * | 10/2013 | Chong ............... A61B 18/1492 606/41 |
| 2016/0095650 | A1 * | 4/2016 | Greifeneder ....... A61B 17/3203 606/41 |
| 2018/0036078 | A1 | 2/2018 | Ditter |
| 2018/0056038 | A1 | 3/2018 | Aujla |
| 2019/0159855 | A1 | 5/2019 | Wittke |
| 2021/0161592 | A1 | 6/2021 | Altmann et al. |
| 2021/0169550 | A1 | 6/2021 | Govari et al. |
| 2021/0169567 | A1 | 6/2021 | Govari et al. |
| 2021/0169568 | A1 | 6/2021 | Govari et al. |
| 2021/0177503 | A1 | 6/2021 | Altmann et al. |
| 2021/0186604 | A1 | 6/2021 | Altmann et al. |
| 2021/0196372 | A1 | 7/2021 | Altmann et al. |
| 2022/0401030 | A1 * | 12/2022 | Bataille ................ A61B 5/6852 |
| 2023/0210433 | A1 * | 7/2023 | Abbas .................. A61B 5/6852 600/509 |

* cited by examiner

MODULAR STEERABLE SHEATH AND CATHETER

FIELD

This disclosure relates generally to medical devices, and in particular to navigation and tracking of intralumenal devices, particularly catheters and guiding sheaths.

BACKGROUND

Cardiac arrhythmias, such as atrial fibrillation (AF), occur when regions of cardiac tissue abnormally conduct electric signals to adjacent tissue. This disrupts the normal cardiac cycle and causes asynchronous rhythm. By selectively ablating cardiac tissue by application of energy via a catheter, it is sometimes possible to cease or modify the propagation of unwanted electrical signals from one portion of the heart to another.

Many contemporaneous ablation approaches utilize radiofrequency (RF) electrical energy to heat tissue. Irreversible electroporation (IRE) is an alternative approach to RF ablation. To achieve IRE, short pulses of high voltage electrical signals (pulse field ablation electrical signals) are delivered to tissues; the electrical signals generate an unrecoverable permeabilization of cell membranes. Delivery of IRE energy to tissues using multi-electrode catheters was previously proposed in the patent literature. Examples of systems and devices configured for IRE ablation are disclosed in U.S. Patent Pub. No. 2021/0169550A1, 2021/0169567A1, 2021/0169568A1, 2021/0161592A1, 2021/0196372A1, 2021/0177503A1, and 2021/0186604A1, each of which are incorporated herein by reference.

Regions of cardiac tissue can be mapped by a catheter to identify the abnormal electrical signals. Some catheter ablation procedures especially those with persistent atrial fibrillation may be performed using electrophysiology (EP) mapping to target areas of aberrant electrical signals. Such EP mapping may include the use of sensing electrodes configured to monitor electrical signals within the cardiovascular system to pinpoint the location of aberrant conductive tissue sites that are responsible for the arrhythmia. Examples of an EP mapping system are described in U.S. Pat. No. 5,738,096, incorporated herein by reference and attached in the Appendix hereto. Examples of EP mapping catheters are described in U.S. Pat. No. 9,907,480, U.S. Patent Pub. No. 2018/0036078, and U.S. Patent Pub. No. 2018/0056038, each of which are incorporated herein by reference and attached in the Appendix hereto.

In addition to using EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, Calif. Examples of catheters that are configured for use with an IGS system are disclosed in U.S. Pat. No. 9,480,416, incorporated herein by reference and attached in the Appendix hereto.

Many catheter-based medical procedures utilize multiple catheters during the medical procedure. In such procedures, a guiding sheath having a lumen therethrough is positioned to provide intravenous access to a treatment site and left in place while catheters and other intralumenal devices (e.g., dilator, transseptal needle, guidewire) are exchanged through the lumen of the guiding sheath. For instance, during a pulmonary vein isolation procedure, a guiding sheath, a diagnostic catheter, and a therapeutic catheter may be utilized. Examples of such devices include, but are not limited to, the CARTO VIZIGOR bi-directional guiding sheath, the OCTARAY™ mapping catheter, and the THERMOCOOL SMARTTOUCH® SF catheter by Biosense Webster, Inc. of Irvine, Calif.

SUMMARY

Systems disclosed herein include a steerable catheter or guiding sheath and modular catheter inserts that can be coupled to the steerable catheter or guiding sheath (herein referred as guiding sheath). The guiding sheath includes a handle that may include an electrical connector configured to couple to an electrical connector of the modular catheter insert so that electrical signals measured at, and/or delivered to a target area pass through the handle of the guiding sheath. The guiding sheath further includes a shaft with a lumen therethrough and may include navigation sensors coupled to a distal portion of the shaft. The catheter insert can be configured to couple to the guiding sheath such that a position of a distal portion of the catheter insert can be determined based on electrical signals from the navigation sensors on the distal portion of the guiding sheath.

The system is configured such that the modular catheter inserts can be interchanged during a medical procedure. For instance, a diagnostic catheter insert and an ablation diagnostic catheter insert can be interchanged during a medical procedure. During a medical procedure, the diagnostic catheter insert can be delivered through the guiding sheath to a target area and the diagnostic catheter can be coupled to the guiding sheath. The location of an end effector of the diagnostic catheter can be determined based on signals from navigation sensor on the distal portion of the guiding sheath. Cardiac electrical signals of the heart can be detected by electrodes disposed on the end effector of the diagnostic catheter insert. The cardiac electrical signals can be transmitted to a computational system via electrical connection between the diagnostic catheter insert and the guiding sheath. The distal portion of the guiding sheath can be articulated to move the end effector of the diagnostic catheter insert across target tissue to detect electrical signals at various locations. The diagnostic catheter insert can then be decoupled from the guiding sheath, and the end effector can be retracted proximally through the shaft of the guiding sheath to decouple the diagnostic catheter insert from the guiding sheath.

During the same medical procedure, the ablation catheter insert can be inserted into the guiding sheath and coupled to the guiding sheath. The location of an end effector of the ablation catheter insert can be determined based on signals from the navigation sensor on the distal portion of the guiding sheath. Electrical signals to ablate tissue can be transmitted through electrical connection between the ablation catheter insert and the guiding sheath base and to the end effector of the ablation catheter insert. The distal portion of the guiding sheath can be articulated to move the end effector of the ablation catheter insert across target tissue to ablate tissue at various locations. The ablation catheter insert can be decoupled from the guiding sheath to allow additional catheter inserts to be coupled to the guiding sheath as needed. The guiding sheath can further be configured to accommodate other intralumenal devices such as a dilator, transseptal needle, and/or guidewire.

One exemplary system can include a guiding sheath and at least one catheter insert. The guiding sheath includes a sheath shaft extending along a longitudinal axis, a handle coupled to a proximal end of the sheath shaft, a first modular electrical port, and a system electrical port. The catheter insert includes a catheter shaft configured to traverse through a lumen of the sheath shaft, a proximal hub coupled to a proximal end of the catheter shaft, an electrode assembly coupled to a distal portion of the catheter shaft, and a second modular electrical port configured to mate with the first modular electrical port of the guiding sheath to pass electrical signals between the electrode assembly and the system electrical port via connection of the first and second modular electrical ports.

An exemplary guiding sheath can include a sheath shaft, a handle, a system electrical port, and a modular electrical port. The sheath shaft extends along a longitudinal axis and has a lumen configured to receive a catheter shaft. The handle is coupled to a proximal end of the sheath shaft. The modular electrical port is configured to electrically connect the system electrical port to an electrode coupled to the catheter shaft.

An exemplary catheter insert includes a catheter shaft extending along a longitudinal axis, a proximal hub coupled to a proximal end of the catheter shaft, an electrode assembly coupled to a distal portion of the catheter shaft, and a modular electrical port configured to mate with an electrical port of a guiding sheath to pass electrical signals between the electrode assembly and the electrical port of the guiding sheath.

An exemplary pulmonary vein diagnostic and treatment kit includes a guiding sheath, a first catheter insert, and a second catheter insert. The guiding sheath includes a sheath shaft extending along a longitudinal axis, a handle coupled to a proximal end of the sheath shaft, a first modular electrical port, and a system electrical port. The first catheter insert includes a first catheter shaft configured to traverse through a lumen of the sheath shaft, a first proximal hub coupled to a proximal end of the first catheter shaft, a first electrode assembly coupled to a distal portion of the first catheter shaft, and a second modular electrical port configured to mate with the first modular electrical port of the guiding sheath to pass electrical signals between the first electrode assembly and the system electrical port via connection of the first and second modular electrical ports. The second catheter insert includes a second catheter shaft configured to traverse through the lumen of the sheath shaft, a second proximal hub coupled to a proximal end of the second catheter shaft, a second electrode assembly coupled to a distal portion of the second catheter shaft, and a third modular electrical port configured to mate with the first modular electrical port of the guiding sheath to pass electrical signals between the second electrode assembly and the system electrical port via connection of the first and third electrical ports.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements. The figures depict one or more implementations of the inventive devices, by way of example only, not by way of limitation.

DETAILED DESCRIPTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

In addition, as used herein, the terms "patient." "host," "user," and "subject" refer to any human or animal subject and are not intended to limit the systems or methods to human use, although use of the subject invention in a human patient represents a preferred embodiment. As well, the term "proximal" indicates a location closer to the operator whereas "distal" indicates a location further away to the operator or physician.

Alternative apparatus and system features and alternative method steps are presented in example embodiments herein. Each given example embodiment presented herein can be modified to include a feature and/or method step presented with a different example embodiment herein where such feature and/or step is compatible with the given example as understood by a person skilled in the pertinent art as well as where explicitly stated herein. Such modifications and variations are intended to be included within the scope of the claims.

Systems and methods disclosed herein are configured to perform a catheter-based medical procedure utilizing multiple catheter inserts.

Figure 1A:
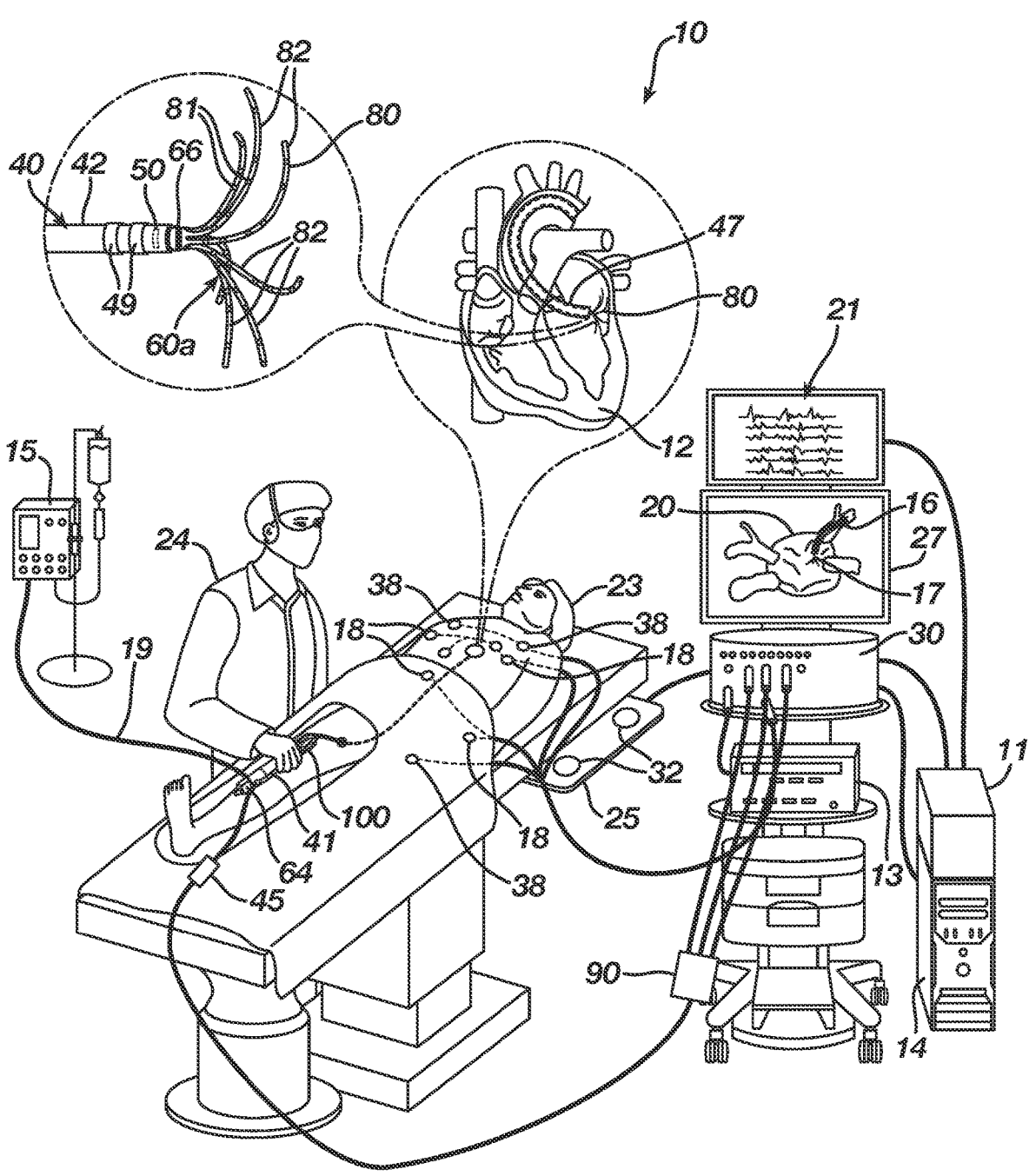
FIGS. 1A and 1B are illustrations of an exemplary catheter-based electrophysiology mapping and ablation system utilizing a modular catheter system.
Figure 1B:
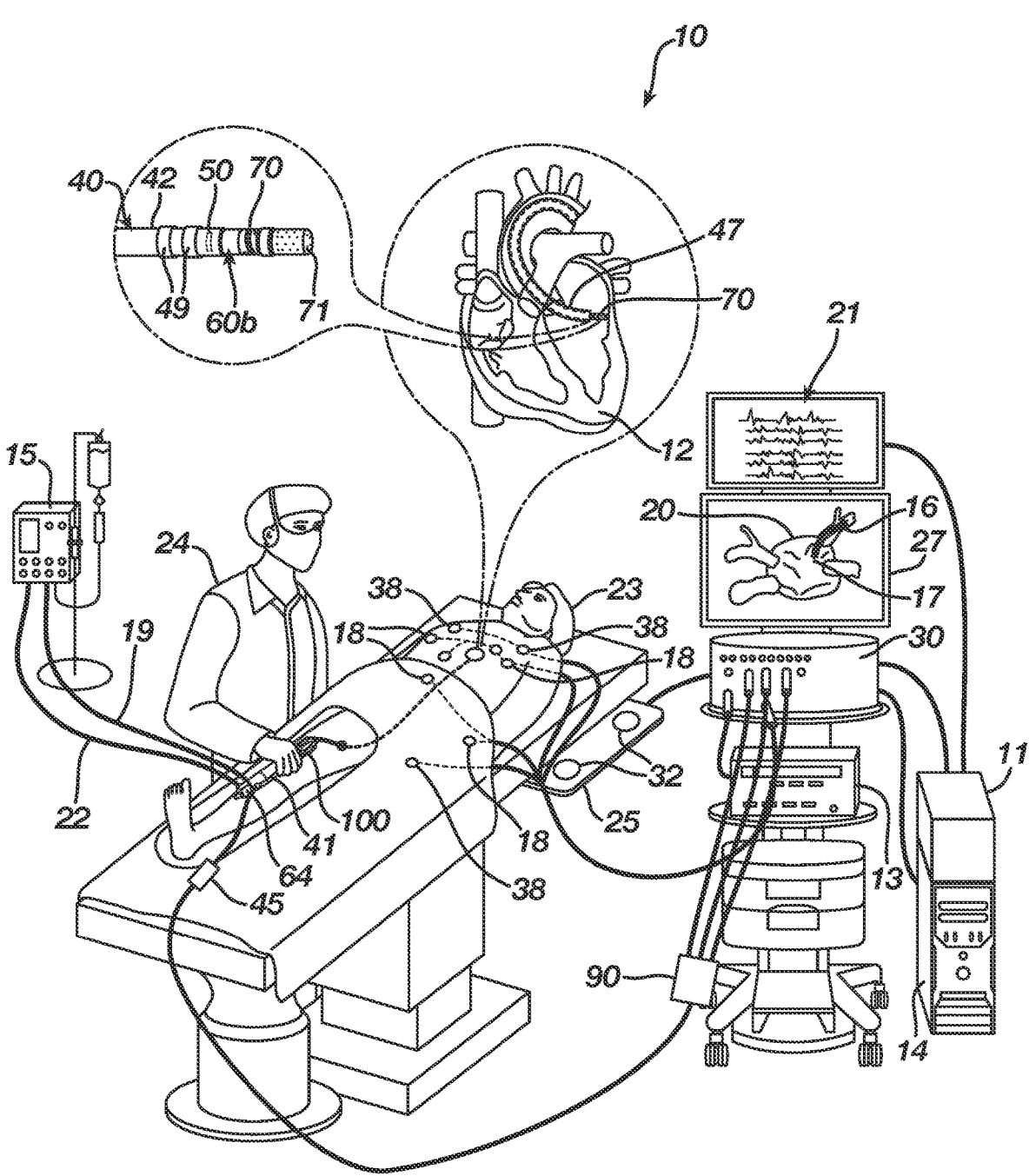

FIGS. 1A and 1B are illustrations of an exemplary catheter-based electrophysiology mapping and ablation system 10 utilizing a modular catheter system 100. FIG. 1A illustrates a diagnostic catheter insert 60a coupled to a guiding sheath 40 at a diagnostic step of a medical procedure, and FIG. 1B illustrates a therapeutic catheter insert 60b (also referred to herein as an ablation catheter insert) coupled to the guiding sheath 40 at a treatment step of the medical procedure.

During a medical procedure, the guiding sheath 40 can be percutaneously inserted by a physician 24 through the patient's vascular system into a chamber or vascular structure of a heart 12. A distal portion of the guiding sheath 40 can be positioned in the left or right atrium near a desired location in the heart 12. Optionally, intravascular devices such as a dilator, transseptal needle, and/or guidewire can be inserted into the guiding sheath 40 to access a target treatment site. Thereafter, the sheath inserts 60a, 60b can be sequentially inserted into the guiding sheath 40 so that an electrode assembly 70, 80 coupled to a distal portion of a shaft of the respective catheter insert 60a, 60b can be brought into contact with tissue at or near the target treatment site. The catheter inserts 60a, 60b can be exchanged during the medical procedure as needed.

The diagnostic catheter insert 60a illustrated in FIG. 1A is configured to sense Intracardiac Electrogram (IEGM) signals. During the diagnostic step, the physician 24 brings the electrode assembly 80 of an end effector of the catheter insert 60a into contact with the heart wall for sensing a target site in the heart 12. The electrode assembly 80 includes one and preferably multiple electrodes 81 optionally distributed over a plurality of spines 82 and configured to sense the IEGM signals.

The ablation catheter insert 60b illustrated in FIG. 1B is configured to provide electrical signal to tissue to ablate tissue and interrupt aberrant electrical signals propagating through heart tissue. The electrode assembly 70 of the ablation catheter insert 60b includes at least one ablation electrode 71. During the ablation step, the physician 24 bring the ablation electrode 71 into contact with tissue of the heart 12 so that ablation energy can be provided to ablation electrode 71 to ablate the tissue.

Referring collectively to FIGS. 1A and 1B, the modular catheter system 100 is configured so that each catheter insert 60a, 60b includes a proximal hub 64 that can be electrically and mechanically coupled to a handle 41 of the guiding sheath 41. The guiding sheath 40 includes a system electrical port 45 configured to provide electrical communication to a patient interface unit (PIU) 30. The patient interface unit (PIU) 30 is an interface configured to establish electrical communication between catheters, electrophysiological equipment, power supply, and a workstation 14 for controlling operation of system 10. Electrophysiological equipment of the system 10 may include for example, the guiding sheath 40, additional catheter inserts, catheters, a location pad 25, body surface ECG electrodes 18, electrode patches 38, an ablation energy generator 13, and a recorder 11. The PIU 30 includes processing capability for implementing real-time computations of location of the modular catheter system 100, for performing ECG calculations, and/or for controlling electrical signals provided to perform ablation. The system 10 can further include an adapter 90 configured to provide electrical connection between the system electrical port 45 and the PIU 30.

During the diagnostic step (FIG. 1A), electrical signals sensed by electrodes 81 of the electrode assembly 80 can be transmitted through conductors in the shaft of the diagnostic catheter insert 60a, through the electrical connection between the proximal hub 64 and handle 41, through the system electrical port 45, through the adapter 90, and to the PIU 30.

The system 10 can include an ablation energy generator 13 that is adapted to conduct ablative energy to one or more of electrodes at a distal tip of a catheter configured for ablating. Energy produced by the ablation energy generator 13 may include, but is not limited to, radiofrequency (RF)

energy or pulsed-field ablation (PFA) energy, including monopolar or bipolar high-voltage DC pulses as may be used to effect irreversible electroporation (IRE), or combinations thereof.

During the ablation step (FIG. 1B), electrical signals can be provided from the ablation energy generator 13, to the PIU 30, through the adapter 90, through the system electrical port 45, through the electrical connection between the proximal hub 64 and the handle 41, through conductors in the shaft of the ablation catheter insert 60b, to the electrode 71 of the electrode assembly 70, and to the target tissue.

Referring collectively to FIGS. 1A and 1B, the guiding sheath 40 includes a navigation sensor 50 coupled to a distal portion of the sheath shaft 42. The navigation sensor 50 is configured for tracking position and orientation of distal portion of the catheter insert 60a, 60b including the respective electrode assembly 70, 80. The navigation sensor 50 is preferably a magnetic based position sensor including three magnetic coils for sensing three-dimensional (3D) position and orientation. A magnetic based position sensor 50 may be operated together with a location pad 25 including a plurality of magnetic coils 32 configured to generate magnetic fields in a predefined working volume. Real time position of the distal portion of the respective catheter insert 60a, 60b may be tracked based on magnetic fields generated with a location pad 25 and sensed by a magnetic based position sensor 50. Details of the magnetic based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091 incorporated by reference herein.

The distal portion of the shaft 42 of the guiding sheath 40 can optionally include electrodes 49 configured to sense electrical signals from the external environment such as fluids and/or tissue. As illustrated, the electrodes 49 may be configured as ring electrodes. The system 10 includes one or more electrode patches 38 positioned for skin contact on the patient 23 to establish location reference for location pad 25 as well as impedance-based tracking of electrodes 49. For impedance-based tracking, electrical current is directed toward electrodes 49 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182 incorporated by reference herein.

The catheter inserts 60a, 60b and guiding sheath 40 can be sized, shaped, and otherwise configured such that when the proximal hub 64 of the respective catheter insert 60a, 60b is coupled the handle 41 of the guiding sheath 40, the respective distal portion of the catheter insert 60a, 60b is at a predetermined position (or approximate predetermined position) in relation to the navigation sensor 50 (and optionally electrodes 49). The PIU 30 can be configured to determine the position of the distal portion of the catheter insert 60a, 60b (and thereby electrodes 71, 81 of the electrode assembly 70, 80 of the respective catheter insert 60a, 60b) based at least in part on the position of the distal portion of sheath shaft 42. The navigation sensor 50 of the sheath shaft is configured to provide an indication of a position of the distal portion of the catheter insert 60a, 60b.

Optionally, the electrodes 71, 81 of a respective catheter insert 60a, 60b may be utilized for impedance-based location tracking of the respective electrode assembly 70, 80. For instance, an electrode assembly can include flexible features, that may be configured to move, within a predefined space, in relation to the navigation sensor 50 (and optionally electrodes 49 on the sheath shaft 42), and imped-ance-based location tracking can be used to determine a location of electrodes within the predefined space. In par-ticular, the electrode assembly 80 illustrated in FIG. 1A includes electrodes 81 coupled to flexible spines 82 each joined to a distal end 66 of the shaft of the diagnostic catheter insert 60a. The flexible spines 82 are able to move within a predefined space near the distal end 66 of the shaft of the diagnostic catheter insert 60a. The distal end 66 of the shaft of the diagnostic catheter insert 60a is at a predeter-mined position in relation to the navigation sensor 50 (and optionally electrodes 49 on the sheath shaft 42), and there-fore the predefined space in which the flexible spines 82 are able to move is at a predetermined position in relation to the navigation sensor 50 (and optionally electrodes 49 on the sheath shaft 42). The electrodes 81 on the spines 82 can be located with impedance-based tracking to provide a more precise location of each electrode 81 within the predefined space.

Because the position of the distal portion of the respective catheter insert 60a, 60b can be determine based on location of the navigation sensor 50 (and optionally electrodes 49 on the sheath shaft 42), the catheter inserts 60a, 60b need not include a navigation sensor. Preferably, the distal portion of the catheter shaft insert 60a, 60b lacks an inductive navi-gation sensor.

As an alternative to the illustrated configuration, the catheter insert 60a, 60b may include an inductive navigation sensor. In such an example, the distal end of the sheath shaft 42 may be determined based at least in part on the inductive navigation sensor of the catheter insert 60a, 60a, and the sheath shaft 42 need not include the illustrated guiding sensor 50. The catheter inserts 60a, 60b and guiding sheath 40 can be sized, shaped, and otherwise configured such that when the proximal hub 64 of the respective catheter insert 60a, 60b is coupled the handle 41 of the guiding sheath 40, the respective distal portion of the catheter insert 60a, 60b is at a predetermined position (or approximate predeter-mined position) in relation to the inductive navigation sensor of the catheter insert. As another alternative, both the guiding sheath shaft 42 and the catheter insert 60a, 60b can include a respective inductive navigation sensor.

The workstation 14 includes memory, processor unit with memory or storage with appropriate operating software loaded therein, and user interface capability. The worksta-tion 14 can be configured to provide multiple functions, optionally including (1) modeling the endocardial anatomy in three-dimensions (3D) and rendering the model or an anatomical map 20 for display on a display device 27; (2) displaying on the display device 27 activation sequences (or other data) compiled from recorded electrograms 21 in representative visual indicia or imagery superimposed on the rendered anatomical map 20; (3) displaying real-time loca-tion and orientation of the distal portion of catheter-based devices within the heart chamber; and (4) displaying on the display device 27 sites of interest such as places where ablation energy has been applied. One commercial product embodying elements of the system 10 is available as the CARTO™ 3 System, available from Biosense Webster, Inc., 31A Technology Drive, Irvine, CA 92618. For instance, the workstation 14 can be configured to provide an end effector visualization 17 that indicates real-time location and orien-tation of a respective electrode assembly 70, 80 and con-figured to provide a sheath visualization 16 that indicates real-time location and orientation of the distal portion of the sheath shaft 42.

A recorder 11 displays electrograms 21 captured with body surface ECG electrodes 18 and intracardiac electro-grams (IEGM) captured with electrodes 26 of the catheter 14. The recorder 11 may include pacing capability for pacing the heart rhythm and/or may be electrically connected to a standalone pacer.

The system 10 may further include an irrigation system 15 configured to provide irrigation fluid to the guiding sheath 40 and/or catheter insert 60a, 60b. The handle 41 of the guiding sheath 40 can be connected to the irrigation system 15 by an irrigation line 19. As illustrated in FIG. 1B, the proximal hub 64 of the ablation catheter insert 60b can be connected to the irrigation system 15 by an irrigation line 22. The modular system 100 can be configured such that irri-gation fluid can be provided to the lumen of the guiding sheath independent of irrigation provided to the ablation catheter insert 60b.

The system 10 may further include an implant and implant delivery system (not illustrated). For instance, a left atrial appendage occlusion (LAAO) device and associated delivery system or other such vascular or cardiac implant and delivery system as understood by a person skilled in the pertinent art. The implant can be delivered with the implant delivery system through the guiding sheath 40 to a treatment site. The navigation sensor 50 can be utilized to determine a position of the sheath distal end 48. The implant can be inserted into the hemostasis valve 51 of the guiding sheath 40, manipulated by the implant delivery system to push the implant distally through the sheath shaft 42, and expelled from the distal end 48 of the guiding sheath 40 at the treatment site. The implant can then be deployed, and the delivery system can be retracted proximally from the guid-ing sheath 40.

Figure 2:
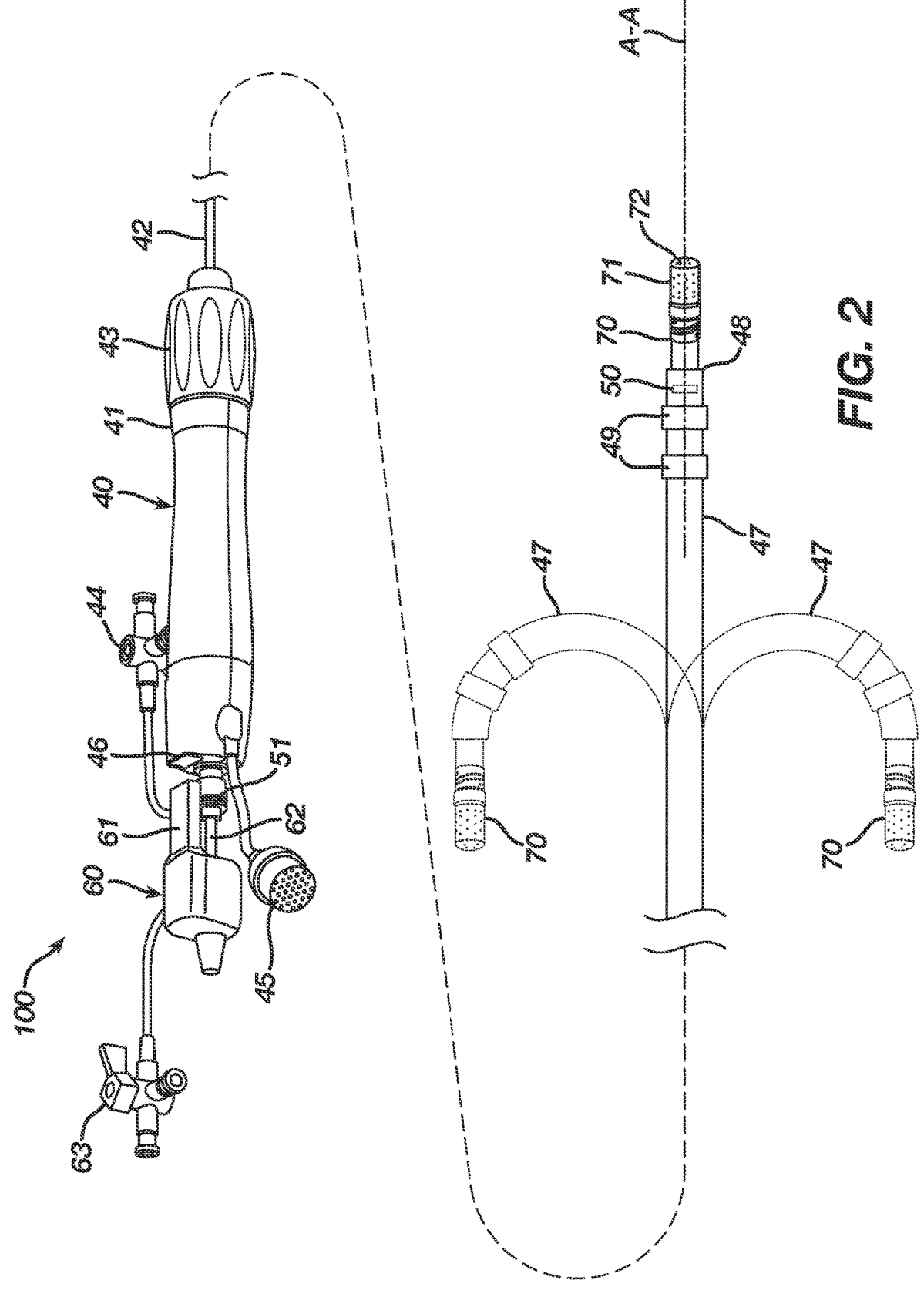
FIG. 2 is an illustration of an exemplary modular catheter system.

FIG. 2 is an illustration of an exemplary modular catheter system 100 including a guiding sheath 40 and a catheter insert 60. The modular catheter system 100 is configured as described in relation to FIGS. 1A and 1B and is illustrated including an ablation catheter insert configured similarly to the ablation catheter insert 60b illustrated in FIG. 1B. The guiding sheath 40 includes a handle 41, a sheath shaft 42 extending distally from the handle 41, a modular electrical port 46, a system electrical port 45, a navigation sensor 50, and ring electrodes 49 configured as disclosed in relation to FIGS. 1A and 1B. The catheter insert 60 includes a proximal hub 60 and an electrode assembly 70 configured as disclosed in relation to FIG. 1B. The modular catheter system 100 can further include a diagnostic catheter insert 60 including an electrode assembly 80 configured as disclosed in relation to FIG. 1A that can be exchanged for the illustrated catheter insert 60.

The guiding sheath 40 includes a first modular electrical port 46, and the catheter insert 60 includes a second modular electrical port 61 configured to mate with the first modular electrical port 46 to pass electrical signals between the electrode assembly 70 and the system electrical port 45. The first and second modular electrical ports 46, 61 may further be configured to mechanically couple to each other to thereby fix a position of the proximal hub 64 in relation to the sheath handle 41. To couple the guiding sheath 40 to the catheter insert 60, a distal end 72 of the sheath insert 60 is inserted into an opening in a hemostatic valve 51 at a proximal end of the sheath handle 41, the shaft 62 of the catheter insert 60 is pushed distally through the sheath shaft 47. Then, the second modular electrical port 61 of the catheter insert 60 is inserted into the first modular electrical port 46 of the guiding sheath 40. Once coupled, a distal portion of the catheter insert 60, including the electrode assembly 70 extends a predetermined length from a distal end 48 of the sheath shaft 47.

The sheath shaft 42 extends along a longitudinal axis A-A. The sheath shaft 42 may be configured to deflect from the longitudinal axis as illustrated. The sheath handle 41 may include a deflection knob 43 configured to be manipulated to deflect the distal portion of the sheath shaft 42 and a distal portion of the catheter shaft 62 from the longitudinal axis. The modular catheter system 100 can be configured such that the distal portion of the catheter shaft 62 is unable to deflect independently from the guiding sheath 40. The catheter insert 60 can lack a mechanism (e.g., puller wires) to deflect the distal portion of the catheter shaft from the longitudinal axis A-A, and the deflection of the sheath shaft 42 alone can be sufficient to position the electrode assembly 70 at desired locations during a medical procedure.

The guiding sheath 40 may further include an irrigation port 44 configured to couple to the irrigation system 15 (FIGS. 1A and 1B). The catheter insert 60 may further include an irrigation port 63 configured to couple to the irrigation system 15 (FIGS. 1A and 1B).

The catheter insert 60 need not include a navigation sensor and associated electrical conductors through the catheter shaft 62, and the catheter insert 60 need not include deflection mechanism such as puller wires. Therefore, the catheter insert 60 can be made cheaper and/or with a smaller French size compared to a respective diagnostic or therapeutic catheter configured with independent navigation and/or deflection. The reduced French size of the catheter insert 60 may further result in the outer diameter of the guiding sheath 40 being smaller than comparable guiding sheaths known in the art, thereby resulting in easier intravenous translation and smaller incision size.

Further, the guiding sheath 40 and catheter insert 60 may be easier to be manipulated by the physician 23 than a comparable system including a guiding sheath and catheter that are independent of each other. When coupled, the proximal hub 64 may essentially act as an extension of the guiding sheath handle 41 so that there is only one handle to manipulate rather than two used in existing procedures. The electrical connection between the guiding sheath 40 and catheter insert allows for a single electrical cable to provide electrical connection to the PIU 30, reducing potential tangle of electrical cables compared to system which have separate electrical cables for the guiding sheath and catheter.

Figure 3A:
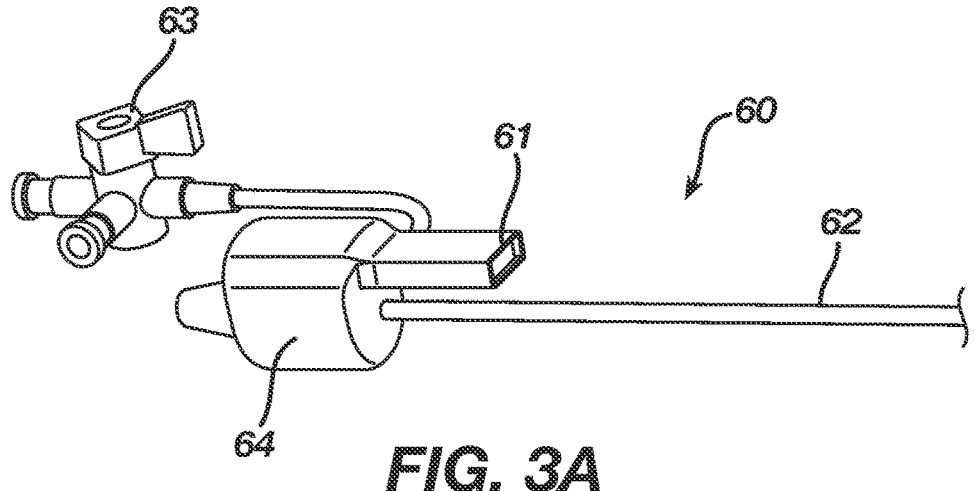
FIG. 3A is an illustration of a proximal portion of an exemplary catheter insert.

FIG. 3A is an illustration of the proximal portion of the exemplary catheter insert 60 showing the proximal hub 64, second modular electrical port 61, and proximal portion of the catheter shaft 62. The catheter insert 60 as illustrated further includes the optional irrigation port 63.

Figure 3B:
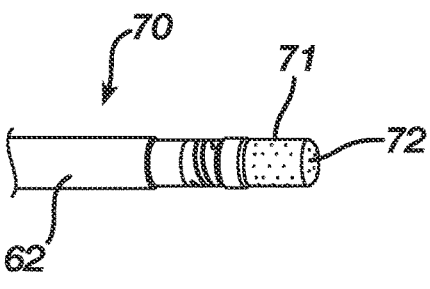
FIG. 3B is an illustration of a distal portion of an exemplary catheter insert.

FIG. 3B is an illustration of a distal portion of an exemplary ablation catheter insert including an electrode assembly 70 with an ablation electrode 71. The ablation electrode 71 is preferably configured to provide irrigation fluid to a treatment site, and therefore the ablation catheter insert preferably includes the irrigation port 63 (FIG. 3A). The ablation catheter insert can include various end effector configurations including balloon, basket, ray, mesh, and other suitable electrode arrangements as understood by a person skilled in the pertinent art.

Figure 3C:
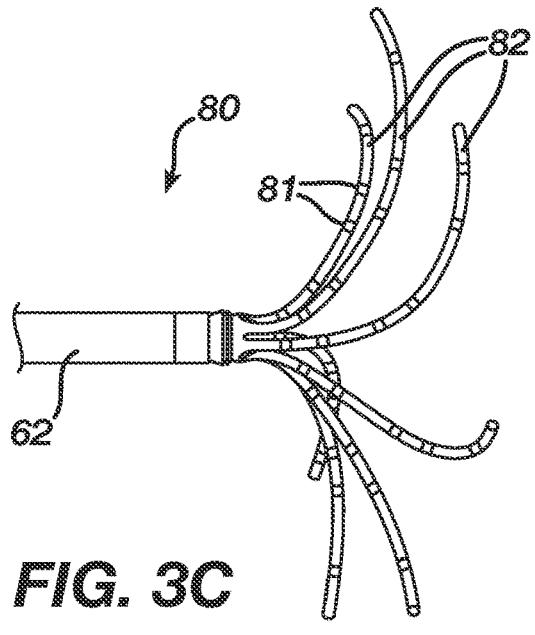
FIG. 3C is an illustration of a distal portion of another exemplary catheter insert.

FIG. 3C is an illustration of a distal portion of an exemplary diagnostic catheter insert including an electrode assembly 80 with electrodes 81 configured to sense IEGM signals. The diagnostic catheter may not require irrigation and therefore may lack the irrigation port 63 (FIG. 3A). The diagnostic catheter insert can include various end effector configurations including balloon, basket, ray, mesh, and other suitable electrode arrangement as understood by a person skilled in the pertinent art.

As another example the catheter insert 60 may be configured to perform visualization of a treatment area. For instance, a visualization catheter insert may include an ultrasound probe approximate a distal end of the visualization catheter. The distal portion of such a visualization catheter insert can be determined as generally described in relation to catheter insert 60.

Figure 4:
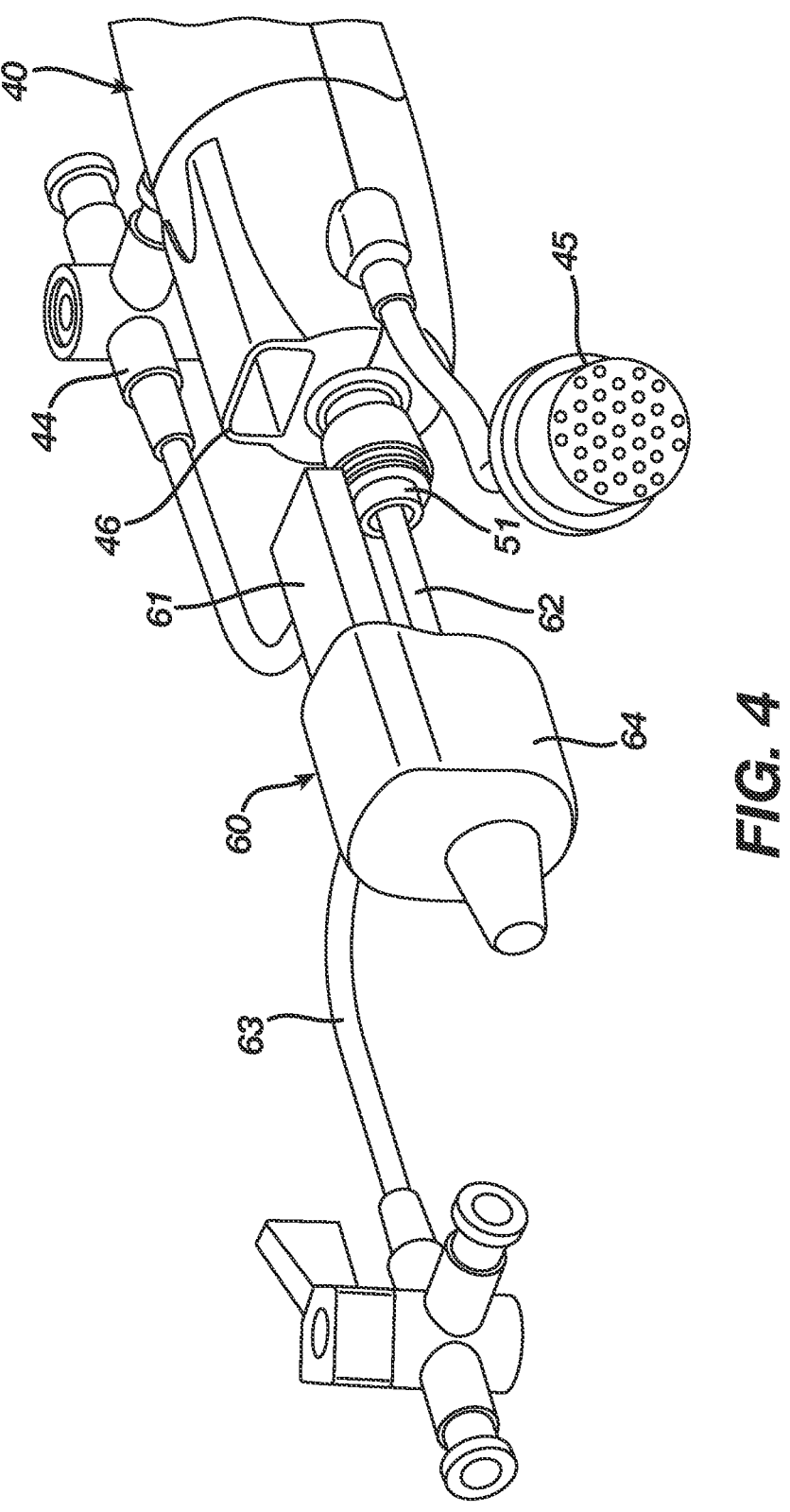
FIG. 4 is an illustration of an isometric view of a proximal portion of the modular catheter system.

FIG. 4 is an illustration of an isometric view of the modular catheter system 100. The shaft 62 of the catheter insert 60 has been inserted into the proximal end of the hemostasis valve 51 of the guiding sheath 40. The catheter insert 60 can be moved in the distal direction in relation to the guiding sheath 40 to mate the second modular electrical port 61 of the catheter insert 60 to the first modular electrical port 46 of the guiding sheath 40.

Figure 5:
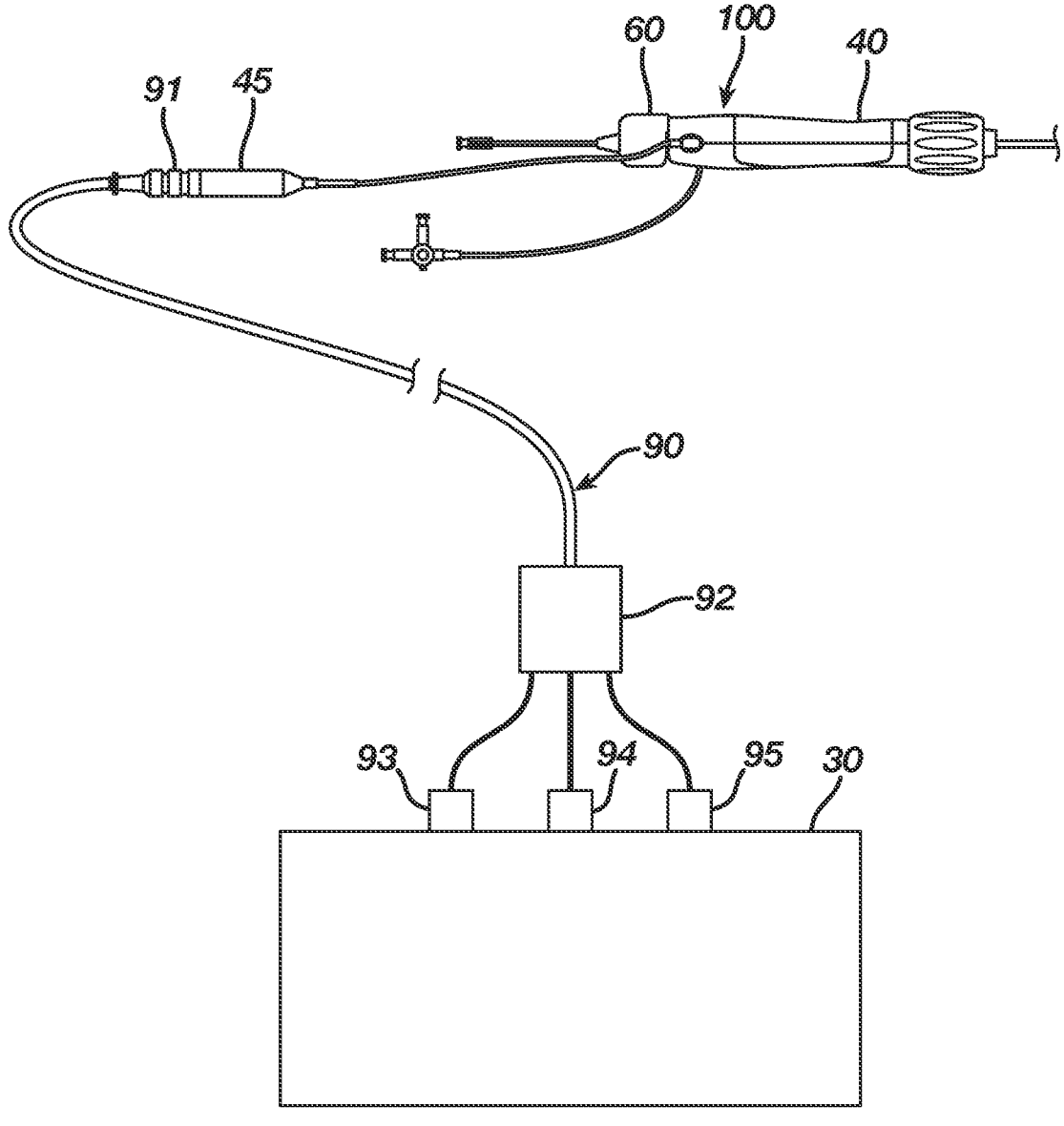
FIG. 5 is an illustration of components of an exemplary catheter-based electrophysiology mapping and ablation system.

FIG. 5 is an illustration of components of an exemplary catheter-based electrophysiology mapping and ablation system configured similarly to the system 10 disclosed in relation to FIGS. 1A and 1B. The adapter 90 includes a sheath electrical connector 91, a splitter 92, a diagnostic electrode connector 93, a mapping connector 94, and an ablation generator connector 95. The sheath electrical connector 91 is configured to electrically couple to the system electrical port 45 of the guiding sheath 40. The diagnostic electrode connector 93 is configured to transmit electrical signals from an electrode assembly of a diagnostic catheter insert to the PIU 30. The mapping connector 94 is configured to electrically couple the navigation sensor 50 (and optionally the electrodes 49) to the PIU 30. The ablation generator connector 95 is configured to electrically couple the ablation electrode(s) 71 to the PIU 30. The splitter 92 is configured to route the electrical signals between the singular sheath electrical connector 91 and the three PIU electrical connectors 93, 94, 95.

Figure 6A:
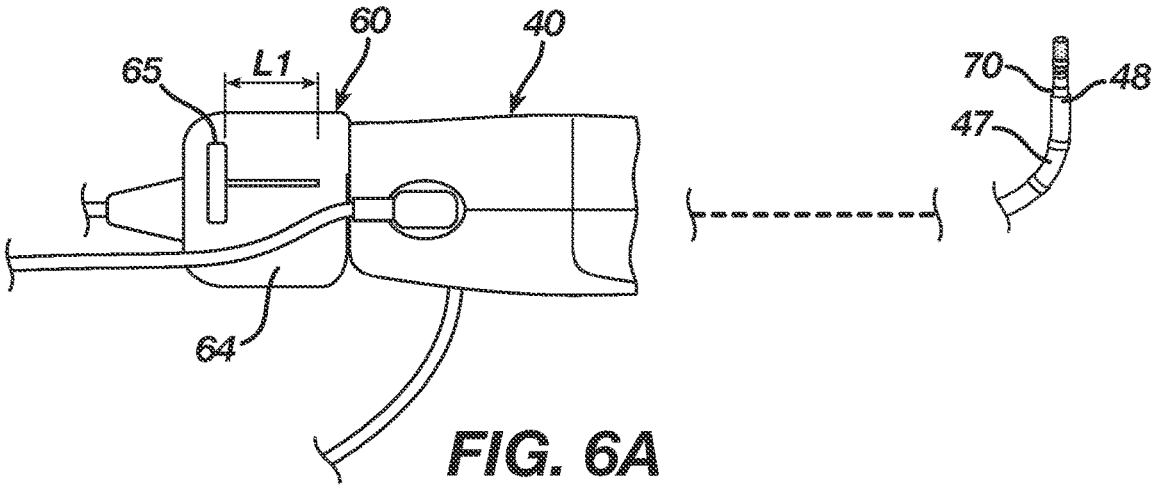
FIGS. 6A and 6B are illustrations of an exemplary modular catheter system including a catheter insert with an adjustable shaft length.
Figure 6B:
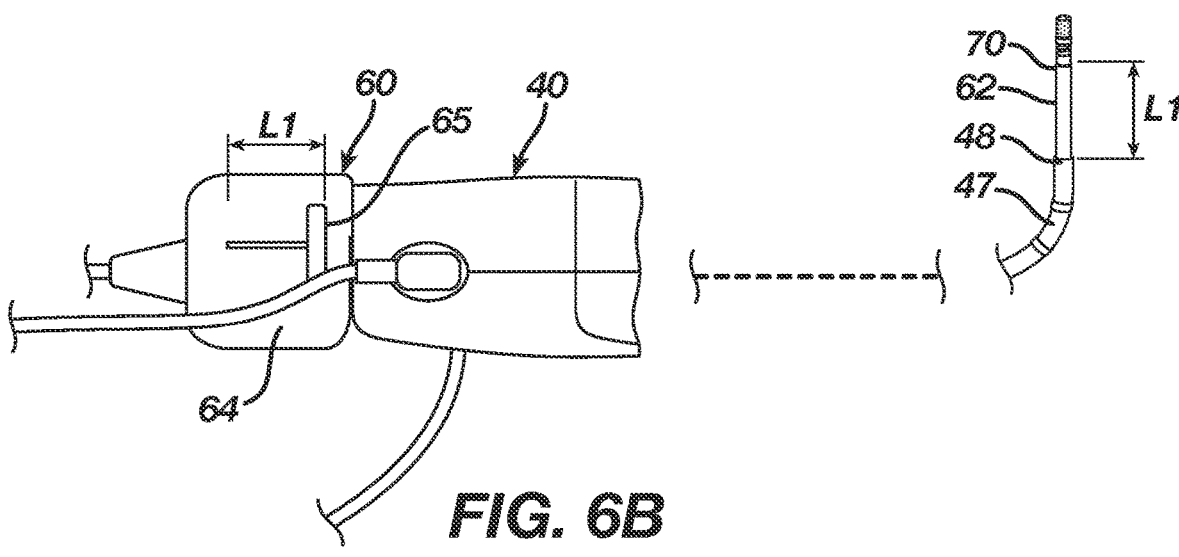

FIGS. 6A and 6B are illustrations of an exemplary assembly including a guiding sheath 40 and a catheter insert 60 with an adjustable shaft length. The proximal hub 64 of the catheter insert 60 includes an extension lever 65 configured to move the catheter shaft 62 proximally and distally by a length L1 so that the catheter shaft 62 can extend and retract by the length L1 from the distal end 48 of the guiding sheath 40. The proximal hub 64 may further be configured with an electrical sensor in electrical communication with the second modular electrical port 61, and the electrical sensor can be configured to provide an electrical signal indicative of length of extension of the distal portion of the catheter insert 60 from the distal end 48 of the guiding sheath 40. The electrical sensor may be electrically coupled to the second modular electrical port 61 (FIG. 4) so that it may be electrically coupled to a computational system, such as the workstation 13 or PIU 30 (FIGS. 1A and 1B) via the connection between the first modular electrical port 46 and the second modular electrical port 61. The computational system can be configured to determine a position of the electrode assembly 70 of the catheter insert 60 based at least in part on the length of extension of the distal portion of the catheter insert 60. The illustrated electrode assembly 70 can have an end effector design similar to existing ablation and/or diagnostic catheters, alternatives thereto, and variations thereof, including those not yet developed, as understood by a person skilled in the pertinent art.

Figure 7:
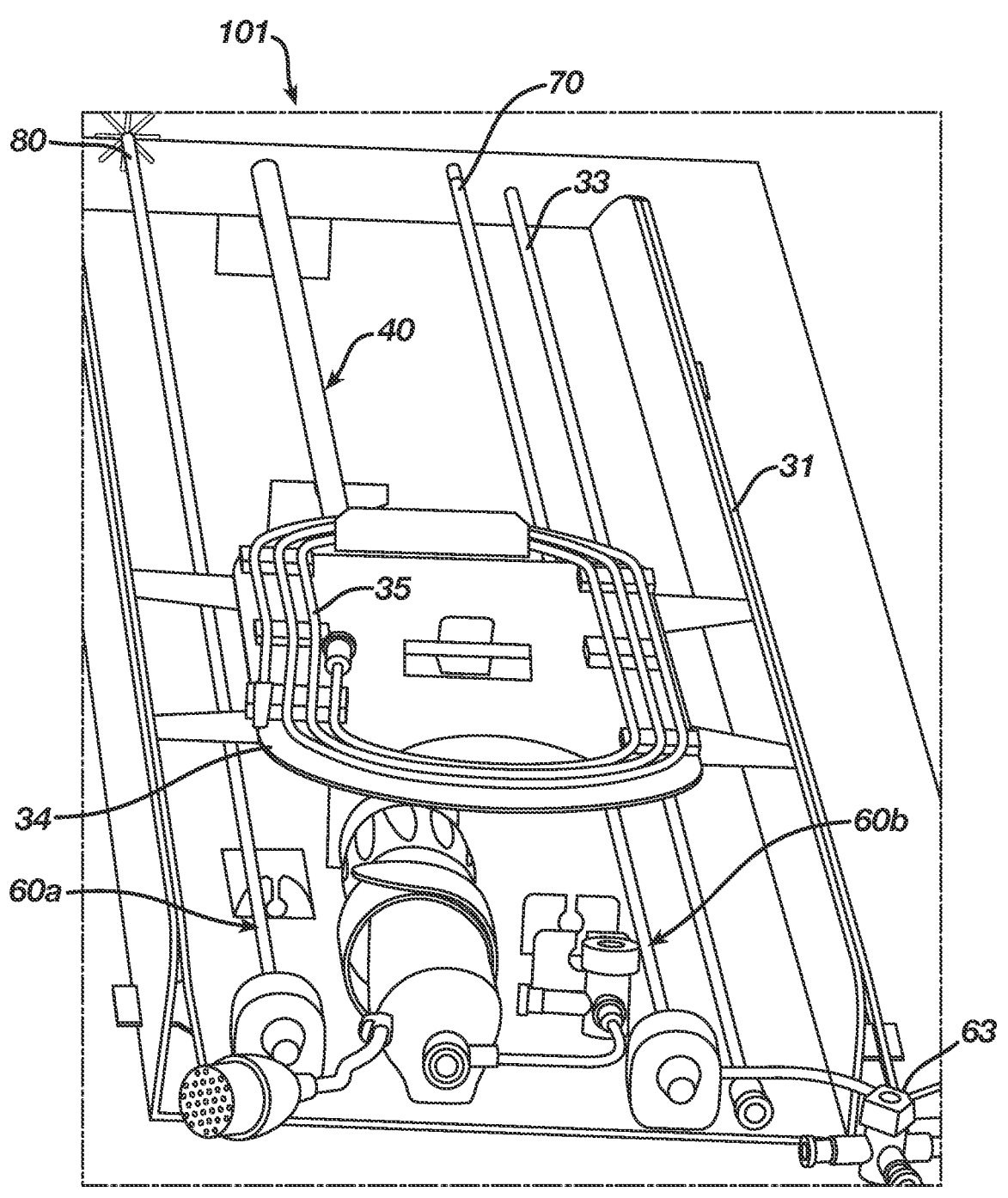
FIG. 7 is an illustration of an exemplary pulmonary vein diagnostic and treatment kit.

FIG. 7 is an illustration of an exemplary pulmonary vein diagnostic and treatment kit 101. The kit 101 includes a guiding sheath 40, a diagnostic catheter insert 60a, and a therapeutic catheter insert 60b configured as disclosed elsewhere herein. The treatment kit 101 can further include accessories such as a dilator 33 and a guide wire 34 (illustrated in a guidewire sheath 35).

The following clauses list non-limiting embodiments of the disclosure:

Clause 1. A system comprising a guiding sheath and a catheter insert, the guiding sheath comprising: a sheath shaft extending along a longitudinal axis; a handle coupled to a proximal end of the sheath shaft; a first modular electrical port; and a system electrical port; and the catheter insert comprising: a catheter shaft configured to traverse through a lumen of the sheath shaft; a proximal hub coupled to a proximal end of the catheter shaft; an electrode assembly coupled to a distal portion of the catheter shaft; and a second modular electrical port configured to mate with the first modular electrical port of the guiding sheath to pass electrical signals between the electrode assembly and the system electrical port via connection of the first and second modular electrical ports.

Clause 2. The system of clause 1, the guiding sheath comprising a navigation sensor coupled to a distal portion of the sheath shaft and in electrical connection with the system electrical port.

Clause 3. The system of clause 2, the navigation sensor being configured to provide an indication of a position of the distal portion of the catheter insert.

Clause 4. The system of any one of clauses 1-3, wherein the distal portion of the catheter shaft lacks an inductive navigation sensor.

Clause 5. The system of any one of clauses 1-4, the handle of the guiding sheath comprising a deflection knob configured to be manipulated to deflect a distal portion of the sheath shaft and a distal portion of the catheter shaft from the longitudinal axis.

Clause 6. The system of any one of clauses 1-5, wherein the catheter insert lacks a mechanism to deflect a distal portion of the catheter shaft.

Clause 7. The system of any one of clauses 1-6, wherein a distal portion of the catheter shaft is unable to deflect independently from the guiding sheath.

Clause 8. The system of any one of clauses 1-7, wherein the first modular electrical port of the sheath insert is coupled to the handle of the guiding sheath, wherein the second modular electrical port of the catheter insert is coupled to the proximal hub of the catheter insert, and wherein the first and second modular electrical ports are configured to mechanically couple to each other to thereby fix a position of the hub in relation to the handle.

Clause 9. The system of any one of clauses 1-8, the handle comprising a hemostatic valve configured to receive the catheter shaft.

Clause 10. The system of any one of clauses 1-9, the guiding sheath further comprising an irrigation port fluidically coupled to the lumen of the sheath shaft.

Clause 11. The system of any one of clauses 1-10, the electrode assembly comprising one or more ablation electrodes configured to ablate cardiac tissue.

Clause 12. The system of clause 11, the one or more ablation electrodes being configured to ablate cardiac tissue using radio frequency ablation electrical signals and/or pulse field ablation electrical signals.

Clause 13. The system of any one of clauses 1-12, the guiding sheath being configured to provide cardiac ablation electrical signals from the system electrical port to the first modular electrical port.

Clause 14. The system of any one of clauses 1-13, further comprising: an ablation generator configured to couple to the system electrical port and provide cardiac ablation electrical signals to the electrode assembly via a connection of the first and second modular electrical ports.

Clause 15. The system of any one of clauses 1-14, the catheter insert further comprising an irrigation port coupled to the proximal hub of the catheter insert and configured to provide irrigation fluid to the distal portion of the catheter shaft.

Clause 16. The system of any one of clauses 1-15, the electrode assembly being configured to sense cardiac electrical signals from cardiac tissue.

Clause 17. The system of any one of clauses 1-16, the electrode assembly comprising a plurality of diagnostic electrodes configured to sense cardiac electrical signals from cardiac tissue.

Clause 18. The system of clause 17, the electrode assembly comprising a plurality of spines configured to transition through the lumen of the guiding sheath in a collapsed configuration aligned to the longitudinal axis and configured to expand away from the longitudinal axis upon exiting a distal end of the guiding sheath, the plurality of diagnostic electrodes being coupled to the plurality of spines.

Clause 19. The system of any one of clauses 16-18, the guiding sheath being configured to receive the cardiac electrical signals at the first modular electrical port and transmit the cardiac electrical signals to the system electrical port.

Clause 20. The system of any one of clauses 1-10, comprising a first catheter insert and a second catheter insert, the first catheter insert comprising said catheter insert, the second catheter insert comprising a second catheter shaft configured to traverse through the lumen of the sheath shaft, a second proximal hub coupled a proximal end of the second catheter shaft, a second electrode assembly coupled to a distal portion of the second catheter shaft, and a third modular electrical port configured to mate with the first modular electrical port of the guiding sheath to pass electrical signals between the second electrode assembly and the system electrical port via connection of the first and third modular electrical ports, and the second electrode assembly comprising an electrode configuration distinct from an electrode configuration of the electrode assembly of the first catheter insert.

Clause 21. The system of clause 20, the electrode assembly of the first catheter insert being configured to ablate cardiac tissue, and the second electrode assembly of the second catheter insert being configured to sense cardiac electrical signals from cardiac tissue.

Clause 22. The system of any one of clauses 1-21, comprising an adapter configured to electrically couple the system electrical port to a computational system and an ablation generator, the computational system being configured to receive cardiac electrical signals from cardiac tissue via the adapter, and the ablation generator being configured to provide ablation electrical signals via the adapter.

Clause 23. The system of clause 22, the guiding sheath comprising a navigation sensor coupled to a distal portion of the sheath shaft and in electrical connection with the system electrical port, and the computational system being configured to determine a position of the distal portion of the sheath shaft based at least in part on navigation electrical signals received from the navigation sensor via the adapter.

Clause 24. The system of any one of clauses 1-23, further comprising: an implant; and an implant delivery system configured to deliver the implant through the guiding sheath to a treatment site.

Clause 25. A guiding sheath comprising: a sheath shaft extending along a longitudinal axis and comprising a lumen configured to receive a catheter shaft; a handle coupled to a proximal end of the sheath shaft; a system electrical port; and a modular electrical port configured to electrically connect an electrode coupled to the catheter shaft to the system electrical port.

Clause 26. The guiding sheath of clause 25, further comprising: a navigation sensor coupled to a distal portion of the sheath shaft, the navigation sensor being in electrical connection with the system electrical port.

Clause 27. The guiding sheath of clause 26, the navigation sensor being configured to provide an indication of a position of the electrode coupled to the catheter shaft.

Clause 28. The guiding sheath of any one of clauses 25-27, the handle comprising a deflection knob configured to be manipulated to deflect a distal portion of the sheath shaft from the longitudinal axis.

Clause 29. The guiding sheath of any one of clauses 25-28, the handle comprising a hemostatic valve configured to receive the catheter shaft.

Clause 30. The guiding sheath of any one of clauses 25-29, further comprising: an irrigation port fluidically coupled to the lumen.

Clause 31. The guiding sheath of any one of clauses 25-30, further comprising: an electrical connection between the system electrical port and the modular electrical port configured to transmit cardiac ablation electrical signals from the system electrical port to the modular electrical port.

Clause 32. The guiding sheath of any one of clauses 25-31, further comprising: an electrical connection between the system electrical port and the modular electrical port configured to transmit cardiac electrical signals from the modular electrical port to the system electrical port.

Clause 33. The guiding sheath of any one of clauses 25-32, where in the modular electrical port is configured such that during a medical procedure, the modular electrical port is configured to electrical couple to a first electrode assembly of a first catheter insert, disconnect from the first electrode assembly of the first catheter insert, and connect to a second electrode assembly of a second catheter insert.

Clause 34. A catheter insert comprising: a catheter shaft extending along a longitudinal axis; a proximal hub coupled to a proximal end of the catheter shaft; an electrode assembly coupled to a distal portion of the catheter shaft; and a modular electrical port configured to mate with an electrical port of a guiding sheath to pass electrical signals between the electrode assembly and the electrical port of the guiding sheath.

Clause 35. The catheter insert of clause 34, wherein a distal portion of the catheter shaft lacks a navigation sensor.

Clause 36. The catheter insert of clause 34 or 35, wherein the catheter insert lacks a mechanism to deflect a distal portion of the catheter shaft.

Clause 37. The catheter insert of any one of clauses 34-36, the electrode assembly comprising one or more ablation electrodes configured to ablate cardiac tissue.

Clause 38. The catheter insert of clause 37, the one or more ablation electrodes being configured to ablate cardiac tissue using radio frequency ablation electrical signals and/or pulse field ablation electrical signals.

Clause 39. The catheter insert of any one of clauses 34-38, further comprising: an irrigation port coupled to the proximal hub and configured to provide irrigation fluid to a distal portion of the catheter shaft.

Clause 40. The catheter insert of any one of clauses 34-39, the electrode assembly being configured to sense cardiac electrical signals from cardiac tissue.

Clause 41. The catheter insert of any one of clauses 34-40, the electrode assembly comprising a plurality of diagnostic electrodes configured to sense cardiac electrical signals from cardiac tissue.

Clause 42. The catheter insert of clause 41, the electrode assembly comprising a plurality of spines configured to transition through a lumen of the guiding sheath in a collapsed configuration aligned to the longitudinal axis and configured to expand away from the longitudinal axis upon exiting a distal end of the guiding sheath, the plurality of diagnostic electrodes being coupled to the plurality of spines.

Clause 43. A pulmonary vein diagnostic and treatment kit comprising a guiding sheath, a first catheter insert, and a second catheter insert, the guiding sheath comprising: a sheath shaft extending along a longitudinal axis; a handle coupled to a proximal end of the sheath shaft; a first modular electrical port; and a system electrical port; the first catheter insert comprising: a first catheter shaft configured to traverse through a lumen of the sheath shaft; a first proximal hub coupled to a proximal end of the first catheter shaft; a first electrode assembly coupled to a distal portion of the first catheter shaft; and a second modular electrical port configured to mate with the first modular electrical port of the guiding sheath to pass electrical signals between the first electrode assembly and the system electrical port via connection of the first and second modular electrical ports; and the second catheter insert comprising: a second catheter shaft configured to traverse through the lumen of the sheath shaft; a second proximal hub coupled to a proximal end of the second catheter shaft; a second electrode assembly coupled to a distal portion of the second catheter shaft; and a third modular electrical port configured to mate with the first modular electrical port of the guiding sheath to pass electrical signals between the second electrode assembly and the system electrical port via connection of the first and third electrical ports.

Clause 44. The pulmonary vein diagnostic and treatment kit of clause 43, wherein the first electrode assembly is configured to ablate tissue, and wherein connection of the first and second modular electrical ports is configured to pass ablation electrical signals from the system port to the first electrode assembly.

Clause 45. The pulmonary vein diagnostic and treatment kit of clause 43 or 44, wherein the second electrode assembly is configured to sense electrical signals from cardiac tissue, and wherein connection of the first and third modular electrical ports is configured to pass the sensed electrical signals from the second electrode assembly to the system port.

Clause 46. The pulmonary vein diagnostic and treatment kit of any one of clauses 42-43, further comprising: a dilator configured to traverse the lumen of the guiding sheath; and a needle configured to traverse a lumen of the dilator.

Clause 47. A method of performing pulmonary vein isolation, the method comprising: positioning a distal portion of a guiding sheath approximate target tissue in a heart; inserting a distal portion of a diagnostic catheter insert into a shaft of the guiding sheath; extending the distal portion of the catheter insert from a distal end of the guiding sheath; coupling a proximal hub of the diagnostic catheter insert to the guiding sheath; determining a position of the distal portion of the diagnostic catheter based at least in part on electrical signals from a navigation sensor coupled to a distal portion of the guiding sheath; sensing cardiac signals with an electrode array of the distal portion of the diagnostic catheter signal; decoupling the proximal hub of the diagnostic catheter insert from the guiding sheath; extracting the distal portion of the diagnostic catheter insert from the shaft of the guiding sheath; inserting a distal portion of an ablation catheter into the shaft of the guiding sheath; coupling a proximal hub of the ablation catheter insert to the guiding sheath; determining a position of the distal portion of the ablation catheter based at least in part on electrical signals from the navigation sensor coupled to the distal portion of the guiding sheath; applying ablation energy to the target tissue with an electrode array of the distal portion of the ablation catheter insert; decoupling the proximal hub of the ablation catheter insert from the guiding sheath; and extracting the distal portion of the ablation catheter insert from the shaft of the guiding sheath.

Clause 48. The method of clause 47, wherein the guiding sheath, the diagnostic catheter insert, and the ablation catheter insert each comprise a respective modular electrical port, wherein coupling the proximal hub of the diagnostic catheter insert to the guiding sheath comprises mating the modular electrical port of the guiding sheath to the modular electrical port of the diagnostic catheter insert, wherein sensing cardiac signals with the electrode array of the distal portion of the diagnostic catheter signal comprises transmitting the cardiac electrical signals through the connection between the modular electrical port of the guiding sheath and the modular electrical port of the diagnostic catheter, wherein coupling the proximal hub of the ablation catheter insert to the guiding sheath comprises mating the modular electrical port of the guiding sheath to the modular electrical port of the ablation catheter insert, and wherein applying ablation energy to the target tissue with an electrode array of the distal portion of the ablation catheter insert comprises delivering electrical signals through the connection between the modular electrical port of the guiding sheath and the modular electrical port of the ablation catheter insert.

Clause 49. The method of clause 47 or 48, comprising: irrigating the ablation catheter and irrigating the guiding sheath independent of each other.

Having shown and described exemplary embodiments of the subject matter contained herein, further adaptations of the methods and systems described herein may be accomplished by appropriate modifications without departing from the scope of the claims. For instance, the distal portions of the illustrated catheter inserts 60, 60a, 60b can have various alternative end effector configurations including balloon, basket, ray, mesh, and other suitable electrode arrangement as understood by a person skilled in the pertinent art. The illustrated electrode assembly 70, 80 can have various alternative end effector designs that may be similar to existing ablation and/or diagnostic catheters, alternatives thereto, and variations thereof, including those not yet developed, as understood by a person skilled in the pertinent art.

In addition, where methods and steps described above indicate certain events occurring in certain order, it is intended that certain steps do not have to be performed in the order described but, in any order, as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

What is claimed is:

1. A system comprising:
   a guiding sheath comprising:
      a sheath shaft extending along a longitudinal axis;
      a handle coupled to a proximal end of the sheath shaft;
      a first modular electrical port coupled to the handle of the guiding sheath; and
      a system electrical port; and
   a catheter insert comprising:
      a catheter shaft configured to traverse through a lumen of the sheath shaft;
      a proximal hub coupled to a proximal end of the catheter shaft;
      an electrode assembly coupled to a distal portion of the catheter shaft; and
      a second modular electrical port coupled to the proximal hub of the catheter insert and configured to mate with the first modular electrical port of the guiding sheath as the catheter shaft is pushed distally through the lumen of the sheath shaft to pass electrical signals between the electrode assembly and the system electrical port via connection of the first and second modular electrical ports.

2. The system of claim 1, the guiding sheath comprising a navigation sensor coupled to a distal portion of the sheath shaft and in electrical connection with the system electrical port.

3. The system of claim 2, the navigation sensor being configured to provide an indication of a position of the distal portion of the catheter insert.

4. The system of claim 1, the handle of the guiding sheath comprising a deflection knob configured to be manipulated to deflect a distal portion of the sheath shaft and a distal portion of the catheter shaft from the longitudinal axis.

5. The system of claim 1, wherein a distal portion of the catheter shaft is unable to deflect independently from the guiding sheath.

6. The system of claim 1,
   wherein the first and second modular electrical ports are configured to mechanically couple to each other to thereby fix a position of the proximal hub in relation to the handle.

7. The system of claim 1, the handle comprising a hemostatic valve configured to receive the catheter shaft.

8. The system of claim 1, the guiding sheath further comprising an irrigation port fluidically coupled to the lumen of the sheath shaft.

9. The system of claim 1, the electrode assembly comprising one or more ablation electrodes configured to ablate cardiac tissue.

10. The system of claim 9, the one or more ablation electrodes being configured to ablate cardiac tissue using radio frequency ablation electrical signals or pulse field ablation electrical signals.

11. The system of claim 1, the guiding sheath being configured to provide cardiac ablation electrical signals from the system electrical port to the first modular electrical port.

12. The system of claim 1, the catheter insert further comprising an irrigation port coupled to the proximal hub of the catheter insert and configured to provide irrigation fluid to the distal portion of the catheter shaft.

13. The system of claim 1, the electrode assembly being configured to sense cardiac electrical signals from cardiac tissue.

14. The system of claim 13, the electrode assembly comprising a plurality of diagnostic electrodes configured to sense cardiac electrical signals from cardiac tissue.

15. The system of claim 14, the electrode assembly comprising a plurality of spines configured to transition through the lumen of the guiding sheath in a collapsed configuration aligned to the longitudinal axis and configured to expand away from the longitudinal axis upon exiting a distal end of the guiding sheath, the plurality of diagnostic electrodes being coupled to the plurality of spines.

16. The system of claim 13, the guiding sheath being configured to receive the cardiac electrical signals at the first modular electrical port and transmit the cardiac electrical signals to the system electrical port.

17. The system of claim 1, comprising a first catheter insert and a second catheter insert, the first catheter insert comprising said catheter insert, the second catheter insert comprising a second catheter shaft configured to traverse through the lumen of the sheath shaft, a second proximal hub coupled a proximal end of the second catheter shaft, a second electrode assembly coupled to a distal portion of the second catheter shaft, and a third modular electrical port configured to mate with the first modular electrical port of the guiding sheath to pass electrical signals between the second electrode assembly and the system electrical port via connection of the first and third modular electrical ports, and the second electrode assembly comprising an electrode configuration distinct from an electrode configuration of the electrode assembly of the first catheter insert.

18. The system of claim 17, the electrode assembly of the first catheter insert being configured to ablate cardiac tissue, and the second electrode assembly of the second catheter insert being configured to sense cardiac electrical signals from cardiac tissue.

19. The system of claim 1, comprising an adapter configured to electrically couple the system electrical port to a computational system and an ablation generator, the computational system being configured to receive cardiac electrical signals from cardiac tissue via the adapter, and the ablation generator being configured to provide ablation electrical signals via the adapter, the guiding sheath comprising a navigation sensor coupled to a distal portion of the sheath shaft and in electrical connection with the system electrical port, and the computational system being configured to determine a position of the distal portion of the sheath shaft based at least in part on navigation electrical signals received from the navigation sensor via the adapter.

20. The system of claim 1, further comprising:

an implant; and an implant delivery system configured to deliver the implant through the guiding sheath to a treatment site.

* * * * *